United States Patent [19]

Himes

[11] Patent Number: 4,503,277

[45] Date of Patent: Mar. 5, 1985

[54] HF REGENERATION IN AROMATIC HYDROCARBON ALKYLATION PROCESS

[75] Inventor: James F. Himes, Mt. Prospect, Ill.

[73] Assignee: UOP Inc., Des Plaines, Ill.

[21] Appl. No.: 556,755

[22] Filed: Nov. 30, 1983

[51] Int. Cl.³ .............................................. C07C 2/64
[52] U.S. Cl. .................................... 585/455; 585/464
[58] Field of Search ............................... 585/455, 464

[56] References Cited

U.S. PATENT DOCUMENTS

| | | | |
|---|---|---|---|
| 3,249,650 | 5/1966 | Fenske | 585/706 |
| 3,494,971 | 2/1970 | Fenske | 585/449 |
| 3,721,720 | 3/1973 | Chapman et al. | 585/723 |
| 3,950,448 | 4/1976 | Witt | 585/449 |
| 3,975,164 | 8/1976 | Brown, Jr. | 422/106 |
| 4,237,327 | 12/1980 | Winter | 585/450 |
| 4,237,328 | 12/1980 | Winter | 585/456 |

Primary Examiner—Curtis R. Davis
Attorney, Agent, or Firm—William H. Page, II; John F. Spears, Jr.

[57] ABSTRACT

A process is disclosed for the production of alkylaromatic hydrocarbons by the HF-catalyzed reaction of an aromatic hydrocarbon with a $C_8$-plus acyclic olefin. The production of linear alkylbenzenes is preferred. The HF is regenerated in a regeneration column in which high boiling compounds are removed from the HF fed to the column. The main stream of HF enters an upper intermediate point in the regeneration column. A second portion of the HF is fed to the top of the regeneration column as reflux. This second portion of HF is withdrawn from the reaction zone rather than from the overhead receiver of the HF regeneration column as in the prior art regeneration method.

12 Claims, 1 Drawing Figure

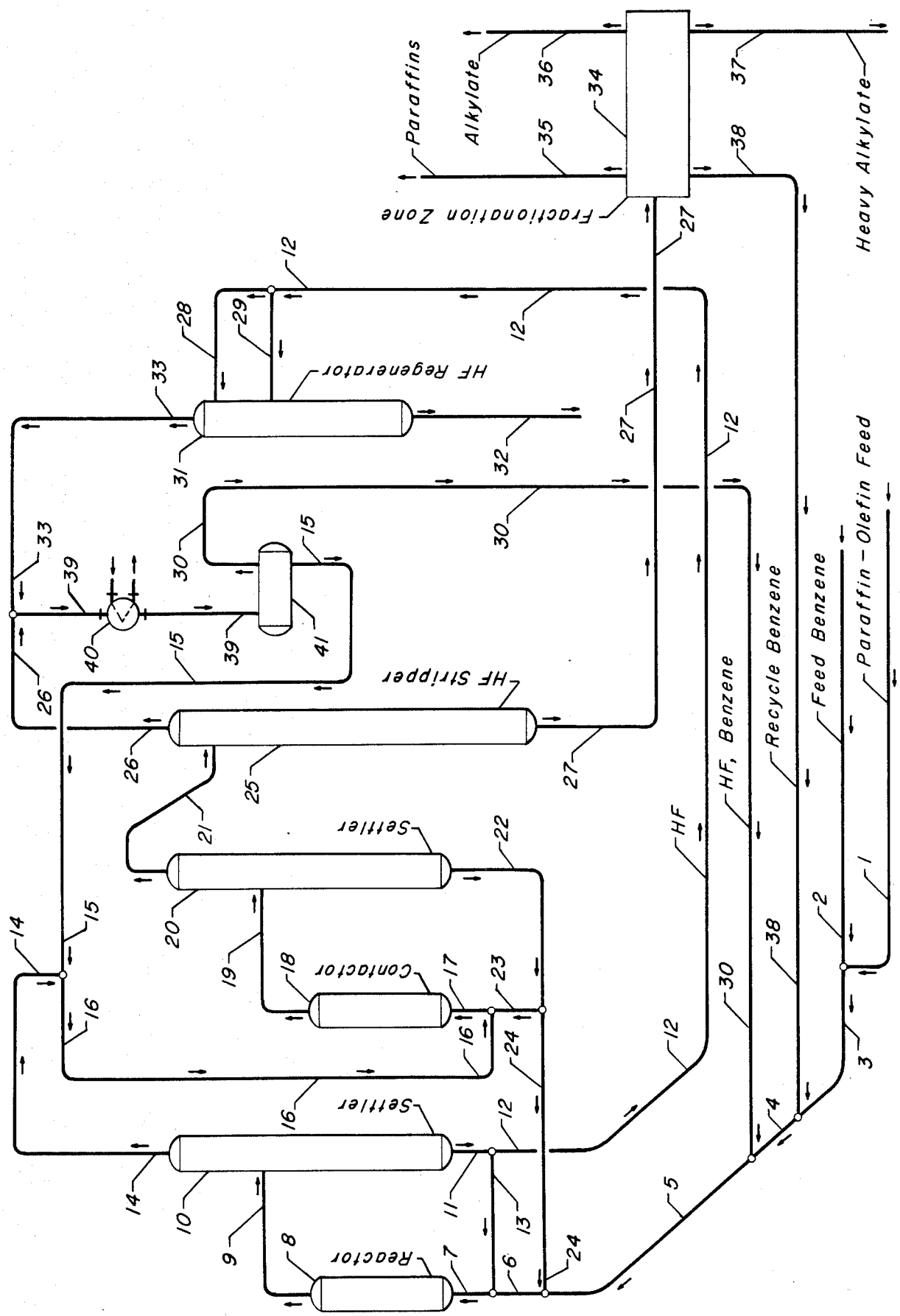

HF REGENERATION IN AROMATIC HYDROCARBON ALKYLATION PROCESS

FIELD OF THE INVENTION

The invention relates to an aromatic hydrocarbon alkylation process. The invention directly relates to a process for the production of alkylaromatic hydrocarbons by the HF catalyzed reaction of an alkylatable aromatic hydrocarbon with an acyclic olefinic hydrocarbon. An example of this is the HF catalyzed alkylation of benzene with a $C_8$-plus normal olefinic hydrocarbon to create a linear alkylbenzene which is highly suitable for the production of detergents. The invention specifically relates to the method utilized to regenerate the HF by removing high boiling hydrocarbonaceous compounds which tend to accumulate in the liquid phase HF. The invention therefore comprises an improved method of regenerating HF used as a catalyst in a hydrocarbon conversion process.

INFORMATION DISCLOSURE

The alkylation of benzene with acyclic olefins is a widely practiced commercial process. This process is performed to produce a variety of chemical compounds which may be end products or may be used as intermediates in the production of other valuable industrial chemicals. One of the most significant processes for the alkylation of aromatic hydrocarbons employs liquid phase HF as the catalyst and is performed to produce linear alkylbenzenes which are then converted into detergents by sulfonation and neutralization. The preferred arrangement of the alkylation zone, suitable reaction conditions, feed materials, and an overall description of an alkylation process of the preferred type is presented in U.S. Pat. No. 3,494,971 issued to E. R. Fenske. This reference is also relevant for its showing of the traditional method of regenerating the liquid phase HF employed as a catalyst in such a "detergent alkylation" process. This regeneration method comprises passing a small stream of HF removed from the initial reaction stage into a stripping column. The HF is removed overhead as a vapor and then condensed leaving a high boiling mass referred to as "tar" which is withdrawn from the stripping column as a net bottoms stream.

U.S. Pat. No. 3,950,448 issued to P. A. Witt and U.S. Pat. No. 4,237,327 issued to G. R. Winter are pertinent for their teaching in regard to the operation and integration of HF regeneration columns into a detergent alkylation process and the possible arrangements of the fractionation zones of detergent alkylation processes. This includes the use of an HF stripping column which receives the entire hydrocarbonaceous effluent stream of the alkylation zone proper. The Winter patent illustrates refluxing the HF regeneration column with a hydrocarbon stream removed from an overhead receiver. U.S. Pat. No. 4,237,328, also issued to G. R. Winter, is believed to be illustrative of the commercial method of refluxing the HF regeneration column. This comprises using as reflux a portion of the liquid phase HF withdrawn from the combined overhead receiver of the HF regeneration column and the HF stripping column.

The regeneration of HF used as catalyst is also practiced in the production of motor fuel by the reaction of isobutane and butylenes. The use of a stripping column to regenerate HF in such s a process is shown in the flow diagram FIG. 2 of U.S. Pat. No. 3,249,650 issued to E. R. Fenske. U.S. Pat. No. 3,721,720 issued to C. C. Chapman et al and U.S. Pat. No. 3,975,164 issued to W. W. Brown, Jr. also describe such alkylation processes but are directed to the apparatus and methods employed in the actual regeneration of the HF.

BRIEF SUMMARY OF THE INVENTION

The invention is an improved method of regenerating HF used as catalyst in an aromatic hydrocarbon alkylation process. The improvement resides in the source of the liquid HF used to reflux the HF regeneration column. In the subject process, the reflux liquid is HF withdrawn from the alkylation reaction zone rather than HF removed from the overhead receiver of the HF regeneration column. This greatly lessens the possibility of hydrocarbons entering the regeneration column in the reflux liquid due to equipment failure in the overhead receiver level control system. These hydrocarbons exit the regeneration column as part of the net bottoms stream and their loss reduces the product yield of the process. The operation of the regeneration column is also improved by a more uniform composition of the reflux liquid.

One embodiment of the invention may be characterized as a process for the production of linear alkylaromatic hydrocarbons which comprises the steps of reacting a feed aromatic hydrocarbon with a $C_6$-plus normal olefinic hydrocarbon in the presence of liquid phase HF having a first purity, and which acts as an alkylation catalyst, in a reaction zone and thereby producing a first hydrocarbon admixture comprising residual feed aromatic hydrocarbon and a product linear alkylaromatic hydrocarbon; contacting said hydrocarbon admixture with liquid phase HF having a higher second purity in a contacting zone and thereby producing a second hydrocarbon admixture comprising the feed aromatic hydrocarbon and the product linear alkylaromatic hydrocarbon; passing the second hydrocarbon admixture into a fractionation zone and recovering the product linear alkylaromatic hydrocarbon from the second hydrocarbon admixture; and regenerating HF withdrawn from the reaction zone in a regeneration column operated at regeneration conditions, with a first aliquot portion of the HF entering the regeneration column at the top of the regeneration column and a second aliquot portion of the HF which is being regenerated entering the regeneration column at a lower point in the regeneration column.

BRIEF DESCRIPTION OF THE DRAWING

The drawing is a simplified process flow diagram of a preferred embodiment of the subject invention. The drawing has been simplified by the deletion of standard process equipment such as startup lines, vessel internals, control systems, reboilers, etc. which may be of the type which is normally employed on a hydrocarbon conversion process of this type. This presentation of one preferred embodiment of the invention is not intended to preclude from the scope of the invention those other embodiments set out herein or which are the result of the normal and reasonable modification of those embodiments.

Referring now to the drawing, a first feed stream comprising an admixture of $C_{10}$-plus paraffins and olefins enters the process through line 1 and is admixed with a second feed stream comprising high purity benzene carried by line 2. These two feed streams pass into line 3 and are admixed with a recycle benzene stream carried by line 38. The resultant admixture of benzene, paraffin, and olefins is carried by line 4 to the junction with line 30, which carries a benzene stream which comprises dissolved hydrogen fluoride. These hydrocarbon streams are passed through line 5 to the junction with line 24 at which they are admixed with liquid HF from the second settler 20 before being passed into line 6. An additional amount of liquid phase HF carried by line 13 is admixed into the material flowing through line 6 to thereby form the total charge stream passed into the reactor 8 via line 7. The reactor 8 is maintained at alkylation-promoting conditions which along with the catalytic effect of the HF promote the reaction between the entering olefinic hydrocarbons and a portion of the benzene fed to the reactor. The reaction products together with unreacted hydrocarbons and HF exit the reactor through line 9 and enter a first settler 10.

The settler 10 is maintained at quiescent conditions which promote the separation of the entering liquids into an upper hydrocarbon phase removed through line 14 and a denser HF phase which is removed through line 11. This HF is divided into a major portion which is recycled to the reactor through line 13 and a smaller portion which is passed to the HF regenerator 31 through line 12. The hydrocarbons flowing through line 14 are admixed with liquid phase HF from line 15, with this admixture passing through line 16 to the junction with line 23. At this point, an additional amount of liquid phase HF from line 23 is admixed into the hydrocarbons to form the charge stream which is passed into the contactor 18 through line 17. The material charged to the contactor is maintained at a high degree of turbulence which results in a treatment of the entering reaction products and the production of an HF-hydrocarbon emulsion removed from the contactor through line 19. This emulsion is passed into a second settler 20. The quiescent conditions maintained within this settler result in the separation of the entering material into an HF phase and a less dense hydrocarbon phase. HF is withdrawn from the settler through line 22 and divided into a portion returned to the contactor through line 23 and a smaller portion which is passed to the reactor through line 24. A hydrocarbon stream is removed from the settler through line 21 and passed into a fractionation column 25 referred to as an HF stripper.

The hydrocarbon stream which enters the HF stripper through line 21 comprises the alkylaromatic hydrocarbons produced in the reactor, unreacted benzene, paraffinic hydrocarbons present in the feed stream of line 1, reaction by-products, and a small amount of HF which is dissolved and possibly admixed with the hydrocarbons. The HF stripper is operated at conditions effective to result in the production of an overhead vapor stream carried by line 26 which comprises essentially all of the HF which enters through line 21 and a portion of the benzene which enters through line 21. This produces a net bottoms stream removed from the HF stripper in line 27 which is essentially free of HF and which contains essentially all of the hydrocarbons charged to the HF stripper except for that portion of the benzene which is withdrawn as part of the overhead vapor. This bottoms stream is passed into a fractionation zone 34 through line 27. The fractionation zone preferably comprises a series of fractionation columns which separate the entering hydrocarbons into a number of high purity streams. A recycle benzene stream removed through line 38 returns unreacted benzene to the reactor. The unreacted paraffins are withdrawn from the process through line 35 and may be passed into a dehydrogenation zone to effect the production of additional olefins for passage into the alkylation process through line 1. The product alkylbenzene is removed through line 36, and a small stream of reaction by-products referred to as heavy alkylate is withdrawn in line 37.

The overhead vapor stream of the HF stripper passes through line 26 into line 39. The overhead vapor stream is passed through the overhead condenser 40 in which the benzene and HF are condensed. The resultant liquids enter the overhead receiver 41 and are separated into a lower HF phase and a less dense upper hydrocarbon phase. The entire HF accumulation in the overhead receiver is removed through line 15 and passed into the contactor. The hydrocarbon phase which is basically benzene with a small amount of dissolved HF is removed through line 30 for passage to the reactor.

The small regeneration stream of HF carried by line 12 is passed into the HF regenerator 31. According to the subject invention, this is performed by dividing the HF to be regenerated into a major portion which enters an upper intermediate point of the HF regenerator through line 29 and a smaller portion which is passed into the top of the regenerator through line 28. The regenerator is operated at conditions which result in entering HF being vaporized and removed as an overhead vapor stream carried by line 33 while the less volatile hydrocarbonaceous contaminants are concentrated into a net bottoms stream removed in line 32. The overhead vapor stream of the HF regenerator is passed through the condenser 40 into the overhead receiver or settler 41.

DETAILED DESCRIPTION

One of the more important commercially performed alkylation reactions is the production of detergent grade alkylated aromatic hydrocarbons. This "detergent alkylate" is normally formed by the reaction of benzene with an olefinic hydrocarbon having from seven to twenty carbon atoms per molecule. A better quality detergent precursor normally results from the use of olefinic hydrocarbons having from about ten to fifteen carbon atoms per molecule. Other applications of the alkylate may lead to different preferred carbon number ranges. The domestic detergents produced from alkylated aromatic hydrocarbons are classified either as "soft" if they meet certain standards of biodegradability or as "hard" if they are relatively non-biodegradable. Soft detergents result from using a long-chain or normal monoolefin as the olefinic reactant. The preferred method of producing these linear olefins is by the dehydrogenation of the corresponding normal paraffins. The dehydrogenation zone may be integrated with the detergent alkylation process as described in U.S. Pat. Nos. 3,413,373, 3,484,498, and 3,494,971. Hard detergents result from the use of branched chain olefins such as propylene tetramer produced in a catalytic condensation process. The use of soft detergents is becoming more widespread, and the subject invention will therefore be discussed priaarily in terms of detergent alkylate intended for the production of soft detergents. The subject process may however be applied to alkylations using such branched olefinic hydrocarbons.

The subject process utilizes hydrogen fluoride (HF) as the catalyst. HF is a very effective alkylation catalyst and one which, through proper selection of reaction conditions, can be made very selective to the desired monoalkylation reaction. Nevertheless, a number of side reactions such as oligomerization do occur. Besides the linking together of two or three of the acyclic feed olefinic hydrocarbons, the side reactions include the dialkylation of the feed aromatic hydrocarbon and the reaction of two or more of the feed aromatic hydrocarbons with a single molecule of the feed olefinic hydrocarbons. This variety of potential reactions results in the production of a very large number of different hydrocarbons being produced as side products, especially when feed olefins having a range of carbon numbers are utilized as one of the feedstocks.

Most of these side product hydrocarbons have rather low volatilities compared to the desired linear alkylbenzenes. They are therefore referred to as "heavy" or high boiling compounds. Some of the side products are soluble in the bulk hydrocarbon streams of the subject process and are removed from the process as a small stream of "heavy alkylate" withdrawn from the terminal fractionation column of the product recovery zone. This is shown for example in the previously cited U.S. Pat. No. 3,950,448. Other side product hydrocarbons are preferentially soluble in the liquid phase HF. These HF-soluble hydrocarbons eventually accumulate in the HF to an undesirably high concentration. The accumulated hydrocarbons begin to reduce the purity of the HF below that which optimizes the performance of the alkylation process. It has therefore become a standard practice to provide an HF regeneration system for the alkylation process, with this system typically comprising a stripping column in which the more volatile HF is separated from the higher boiling side product hydrocarbons. The bottoms product is often referred to as "tar" in a process for the production of alkylaromatic hydrocarbons or as acid-soluble oil in an alkylation process for the production of motor fuel.

In the regeneration of HF in a distillation column, the HF is separated from the less volatile contaminants by vaporizing the HF and removing it as the overhead vapor stream of the regeneration column. The overhead vapor is passed through a condenser in which the HF is liquefied, and the resultant liquid is collected in an overhead receiver or settler. It is customary to employ a common overhead condenser and receiver for the HF regeneration column and the larger HF stripping column since this results in a more economical process. The overhead vapor stream of the HF stripping column contains both HF and benzene. Therefore, significant amounts of both liquid HF and liquid benzene enter the overhead receiver. It is necessary to draw off these liquids separately, and the liquids are therefore separated by decantation in the overhead receiver. This is a very severe operational environment for the level or interface controller used to control the removal of the denser HF phase. It is also difficult to monitor the level of the HF-hydrocarbon interface. When the controller fails to maintain a sufficient HF level in the receiver, hydrocarbons are included in the liquid stream removed from the HF drawoff point. When a part of this stream is used to reflux the regeneration column, as has heretofore been practiced, hydrocarbons are thereby charged to the regeneration column. This can upset the operation of the regeneration column. More importantly, hydrocarbons fed to the regeneration column will tend to become part of the net bottoms stream of the column, which is sent to disposal facilities. Misoperation or a failure of the level control system of the receiver can therefore result in the loss of valuable benzene or other hydrocarbons.

It is an objective of the subject invention to provide an improved process for the HF-catalyzed alkylation of aromatic hydrocarbons. It is a specific objective of the invention to provide an improved method of regenerating used HF in a process for the alkylation of benzene.

The aromatic hydrocarbon which is alkylated in the subject process is preferably benzene, but may be a higher molecular weight aromatic hydrocarbon. The feed aromatic hydrocarbon may therefore be toluene, a xylene, ethylbenzene, phenol, naphthalene, etc. The feed olefinic hydrocarbon which is consumed in the process may have from about six to twenty carbon atoms per molecule. A $C_{10}$ to $C_{15}$ olefinic hydrocarbon is preferred for the production of detergent alkylate used in soaps or laundry detergents. The preferred olefinic hydrocarbons are straight-chain monoolefins having from ten to fifteen carbon atoms per molecule. When these olefinic hydrocarbons are produced in a dehydrogenation process which is integrated with the alkylation process, it is a common practice to pass the unseparated paraffin/olefin mixture produced as the effluent of dehydrogenation process into the alkylation process as the olefin-containing feed stream. This is basically because of the high cost of separating olefins and paraffins of the same carbon number, but the presence of the paraffins can also be beneficial, as by decreasing the overall olefin concentration. The olefin-containing feed stream charged to the alkylation process may therefore contain from about 30 to about 85 mole percent of straight chain paraffins having the same number of carbon atoms per molecule as the olefinic hydrocarbons. These relatively non-reactive paraffins pass through the alkylation process in the various hydrocarbon phase streams and are eventually separated from the alkylate by fractionation and then recycled to the dehydrogenation process.

Chemical reactions which involve olefinic hydrocarbons and are catalyzed by hydrogen fluoride usually proceed at a very fast rate. To reduce the amount of olefin polymerization and to promote the production of a monoalkylated aromatic product, the reactants are normally subjected to vigorous mixing and agitation at the point of initial contact of the olefinic hydrocarbons and the liquid phase hydrogen fluoride. The desired result is a uniform dispersion and intimate contacting of the hydrocarbon and hydrogen fluoride phases and the avoidance of localized high temperatures or localized high concentrations of either the olefinic hydrocarbon or the hydrogen fluoride. The initial contacting of the reactants and the catalyst has been done in a number of different ways. For instance, the olefinic hydrocarbons have been sprayed into a mixture of hydrogen fluoride and hydrocarbons through nozzles, and mixtures of the reactants have been released into eductors as high velocity streams which cause the eduction and admixture of the hydrogen fluoride. U.S. Pat. No. 4,134,734 describes a unitary reactor for the production of detergent alkylate. U.S. Pat. No. 4,072,730 describes a process for producing detergent alkylate in which a centrifugal pump is utilized as the first reaction zone due to the intense agitation which occurs within the pump.

The alkylation zone preferably has an overall arrangement similar to that shown in previously referred to U.S. Pat. No. 3,494,971. In this arrangement, the two feed hydrocarbon streams and liquid phase HF are charged to a reactor. The effluent of this reactor is passed into a first settling zone and separated into HF and hydrocarbon phases. The settling zones are preferably elongated horizontal vessels rather than the vertical illustrated in the Drawing. The HF is withdrawn and divided into a first portion passed into the HF stripping column for regeneration and a second portion returned to the reactor. The hydrocarbon phase is withdrawn from the first settling zone and charged to a contactor, which is sometimes referred to as the second "reactor", as the only hydrocarbon charged to the contactor. The HF charged to the contactor is a mixture of newly regenerated HF and HF withdrawn from a second settling zone, which receives the total effluent of the contactor. A portion of the HF withdrawn from the second settling zone is charged to the reactor to replace the HF withdrawn for regeneration. The hydrocarbon phase which is withdrawn from the second settling zone may be withdrawn as an alkylation zone effluent stream but is preferably passed into a stripping column in which dissolved HF is removed overhead and some of the feed aromatic hydrocarbon is also recovered. The net bottoms of this HF stripping column is charged to the fractionation or other product recovery zone employed in the process.

The alkylation reaction zone and the contacting zone are maintained at alkylation-promoting conditions. As used herein, the term "alkylation-promoting conditions" is intended to include a pressure sufficient to maintain the reactants and HF in a liquid phase. A general range of operating pressures is from about 2 to 41 atmospheres absolute. The temperature range covered by this set of conditions is from about $-20°$ to about $95°$ C., but the reaction is preferably conducted at a temperature of from $15°$ to $50°$ C. The volumetric ratio of HF to the total amount of hydrocarbons entering the first reaction zone should be maintained within the broad range of from about 0.2:1 to about 10:1. A preferred range for this ratio is from 1:1 to 2.5:1. To lessen the production of polyalkylated benzenes and to reduce the amount of olefin polymerization in the first reaction zone, the mole ratio of benzene to the monoolefin at the point of initial olefin-acid contact is maintained above 1:1, but preferably below 10:1. A range of typical commercial ratios is from 3:1 to about 8:1.

The conditions maintained within the contacting zone are similar to the conditions maintained in the reaction zone, but some adjustment is required. For instance, since essentially all of the olefin is preferably consumed in the reaction zone, the hydrocarbon stream fed to the contacting zone is substantially free of olefins. There is therefore no benzene to olefin ratio to be specified. The same pressure range may be used in the contacting zone as in the reaction zone, but a higher temperature is preferred. This higher temperature should be at least 6 to 10 Centigrade degrees above that used in the reaction zone. All temperatures specified herein are intended to refer to the average temperature of the liquid stream entering the respective zone.

The HF/hydrocarbon ratio maintained in the contacting zone will normally be slightly lower, and a typical ratio is about 1:1. The purity of acid used in the contacting zone will, however, be higher. This is preferred because of the greater effectiveness of higher purity acid for the treatment of the alkylate. This treatment consists of the defluorination of the alkylate product and the extraction of naphthalenes and anthracenes. A higher acid purity is obtained by admixing the newly regenerated acid into the alkylate-containing hydrocarbon stream entering the contacting zone. The recycle acid for use in the reaction zone is withdrawn from the second settling zone and therefore contains a higher concentration of high molecular weight hydrocarbonaceous impurities. The acid used in the reaction zone preferably contains about 85–92 wt. % HF and will typically be about 90 wt. % HF. The acid used in the contacting zone preferably contains more than 90 wt. % HF and is typically about 93–94 wt. % HF.

The effluent streams leaving the reaction zone and the contacting zone will typically be an intimate admixture of liquid phase hydrocarbons and liquid phase hydrogen fluoride. They may be in the form of a true emulsion. A considerable residence time is normally required to separate these two liquid phases, and the effluent streams are therefore passed into quiescent settling zones. The two settling zones will normally be maintained at a temperature which is set by the entering HF-hydrocarbon mixtures withdrawn from the respective upstream zones. They will therefore be at substantially the same temperature as the immediately upstream reaction or contacting zone. The same is also normally true for the pressures used in the settling zones after adjustaent for any pressure change due to liquid flow and elevation differences. The settling zones may however be downstream of control valves and therefore operated at a somewhat reduced pressure. This reduced pressure, however, must be superatmospheric and sufficient to maintain liquid phase conditions. A residence time for both the acid and hydrocarbon phases in the settling zones should be in excess of 90 seconds but less than 30 minutes.

As previously stated, the hydrocarbonaceous phase removed from the second settling zone is preferably passed into a fractionation column commonly referred to as the HF stripping column. This column derives its name from its basic function in the prior art of preventing the passage of HF into the downstream fractionation zone. Representative conditions for the operation of the HF stripping column include an overhead vapor temperature of about $250°$ F. at a pressure of approximately 36 psig. There is normally no external reflux to this column. The overhead vapor stream of the HF stripping column is normally completely condensed by cooling it to about $100°$ F. or less and is then decanted and recirculated as described above. The entire hydrocarbonaceous effluent of the second settling zone is normally passed onto the top tray of this column. The net bottoms stream of this column contains the product alkylate.

The previously cited patents also describe fractionation systems and conditions suitable for use as an effective separation zone to recover the product alkylate from the bottoms stream of the HF stripping column. For instance, the bottoms stream of the HF stripping column is preferably passed into a second fractionation column referred to as a benzene column. The benzene column is operated under conditions effective to cause the division of the entering hydrocarbons into a high purity benzene stream which is removed as the overhead liquid and a bottoms stream containing the alkylate product. This bottoms stream is passed into a third fractionation column referred to as a paraffin column. The non-reactive paraffins are removed as an overhead liquid stream. The bottoms stream of the third fractionation column comprises the product alkylate and the higher molecular weight side product hydrocarbons formed in the reaction zone. This bottoms stream is passed into a fourth fractionation column which produces a high purity overhead stream containing the detergent alkylate. A bottoms stream comprising polymerized olefins and polyalkylated benzenes (heavy alkylate) is removed from the fourth column for disposal. The third and the fourth fractionation columns are normally operated at a subatmospheric pressure. An alternative method of performing this separation is disclosed in previously cited U.S. Pat. No. 3,950,448. In this arrangement, the bottoms stream of the HF stripping column is passed into a column referred to as a paraffin column. All of the feed aromatic hydrocarbon is withdrawn from the HF stripping column in an overhead stream or as a liquid stream removed below a contact condenser located in the top of the column. The net bottoms stream of the HF stripping column is therefore devoid of the feed aromatic hydrocarbon. This bottoms stream is then separated in the same manner as set out above.

A small portion of the HF used in the reaction zone is preferably passed into a regeneration column on a continuous basis. The subject invention comprises "refluxing" the HF regeneration column with liquid phase HF withdrawn from the reaction zone. The source and composition of the reflux liquid is therefore the same as the main feed stream to the HF regeneration column. As used herein, the term "reflux" and similar terms is intended to indicate liquid, other than the main feed stream, charged to the top of a distillation column to aid in the desired separation of the components of the feed stream. This definition is required since the material used to reflux the column has not been removed from the column and is therefore not being returned to the column as in the case of true reflux liquid.

The main feed stream to the HF regeneration column enters the column at a lower point below the top of the column. The contacting equipment employed within the regeneration column preferably comprises vapor-liquid contacting trays but the column may contain various types of packing material instead. Preferably, the contacting devices located between the top of the column and the feed point are sufficient to provide at least three theoretical or ideal contacting stages above the feed point to the column. The HF passed into the regeneration column is preferably removed from the first settling zone which receives the effluent of the reactor. The HF level in this vessel is normally quite constant due to the significant amounts of HF present and the fact that a great majority of the HF is retained in the circulating loop of the HF flow compared to the small rates of HF addition and withdrawal. Furthermore, the rate at which HF is removed for regeneration is normally set at a constant rate which is balanced by the rate of HF addition from the contacting stage. The HF may therefore be supplied to the regeneration column at a constant rate and with a very uniform composition. The great majority of this regeneration stream enters the regeneration column at the feed point, with the remainder being used as reflux. Preferably, the feed portion of the HF is at least twice as large as the portion of the HF used as reflux. More preferably, the reflux portion of the regeneration HF stream is equal to between 10 and 35 wt. % of the total regeneration HF stream. The reflux portion of the HF may normally be passed into the regeneration column at the temperature at which it is withdrawn from the first settling zone. Preferably, the remaining feed portion of the regeneration HF stream is heated prior to being charged to the regeneration column.

A preferred embodiment of the subject process may therefore be characterized as comprising the steps of admixing a feed aromatic hydrocarbon with an acyclic feed olefinic hydrocarbon which has more than eight carbon atoms per molecule and with liquid phase HF in a reaction zone maintained at alkylation-promoting conditions and thereby forming a reaction zone effluent stream which comprises the feed aromatic hydrocarbon, HF, a product alkylaromatic hydrocarbon, and a small amount of high boiling reaction by-products; separating substantially all of the hydrocarbons present in the reaction zone effluent stream from the liquid phase HF present in the reaction zone effluent stream, and thereby forming a first hydrocarbon stream and a first HF stream, passing the thus-derived first hydrocarbon stream into a contacting zone wherein the first hydrocarbon stream is contacted with liquid phase HF having a higher purity than the HF which is employed in the reaction zone and thereby forming a contacting zone effluent stream which comprises the feed aromatic hydrocarbon, HF, and the product alkylaromatic hydrocarbon; separating substantially all of the hydrocarbons present in the contacting zone effluent stream from the liquid phase HF present in the contacting zone effluent stream and thereby forming a second hydrocarbon process stream and a second HF stream; passing a first portion of the second HF stream into the contacting zone and a second portion into the reaction zone; dividing the first HF stream into a first HF recycle stream, which is passed into the reaction zone, and a regeneration HF stream; passing a first aliquot portion of the regeneration HF stream into an HF regeneration column operated at HF regeneration conditions at the upper end of the regeneration column, and passing a larger second aliquot portion of the regeneration HF stream into the HF regeneration column at a second lower point; and recovering the product alkylaromatic hydrocarbon from the second hydrocarbon process stream.

The following example is presented to further illustrate the subject process. It is based on the result of engineering calculations used to design a commercial scale process unit rather than measurements from an operating unit. The overall flow scheme of the process unit is similar to that shown in the Drawing and other portions of the process operate in a standard commercial mode. A stream of regeneration HF is withdrawn from the first settling vessel at a flow rate of about 6525 lbs/hr or approximately 306 moles/hr. A reflux stream having a flow rate of about 1305 lbs/hr is passed onto the top tray of the twelve-tray HF regeneration column. The remaining 5220 lbs/hr is first heated to approximately 145° F. (63° C.) and is then passed into the regeneration column at the seventh tray from the top of the column. The regeneration column is operated with a bottoms liquid temperature of approximately 270° F. (132° C.) at a pressure of about 43 psig. An overhead vapor stream having a flow rate of approximately 6175 lbs/hr is removed from the regeneration column at a temperature near 143° F. (62° C.). This overhead vapor is combined with the overhead stream of the HF stripper and cooled to about 100° F. in an overhead condenser. The resultant liquids are passed into a settling vessel. A liquid phase HF stream having a flow rate of about 6440 lbs/hr is removed from the settling vessel and passed into the contacting zone. This HF stream has a high purity due to the removal of high boiling materials drawn off the bottom of the regeneration column.

The product linear alkylbenzene of the preferred embodiment is a suitable raw material or feedstock for the preparation of a true detergent or surface active agent. Excellent detergents may be produced from the alkylbenzene through sulfonation to produce a sulfonic acid derivative by contact with an agent such as sulfur trioxide. This derivative is then neutralized by passage into a saponification zone. The neutralization comprises the admixture of the sulfonation reactor effluent with an aqueous stream containing ammonia, sodium hydroxide or potassium hydroxide. The alkaline compound neutralizes the sulfonic acid to produce sulfonates such as water-soluble sodium alkylaromatic monosulfonate salts. Further information on sulfonation and saponification are available from many standard references and from U.S. Pat. Nos. 4,036,875 and 4,240,978. The product alkylate can also be subjected to other chemical reactions to produce other types of detergents. For instance, the alkylate may be nitrated to form a substituted mono-nitro derivative which is then catalytically reduced to a mono-amino-substituted analog such as an alkylaniline or alkyltoluidine. The amine is then condensed with ethylene oxide or propylene oxide to introduce a hydrophilic polyoxyalkylene group on the amino nitrogen atom. This preferably forms a polyoxyalkylated detergent product having from about 10 to 30 oxyalkylene units per molecule. The condensation may be catalyzed by the presence of an alkaline catalyst such as sodium hydroxide.

The normal paraffin stream which is preferably produced in the fractionation zone is preferably passed into a catalytic paraffin dehydrogenation zone. In this zone, the paraffins in admixture with hydrogen are contacted with a catalyst at an elevated temperature to produce additional feed olefinic hydrocarbons. A preferred set of dehydrogenation conditions includes a temperature of about 420° to about 545° C., a pressure from about 0.7 to about 13 atmospheres (preferably about 2.0), and a liquid hourly space velocity in the range of about 10 to 36. A catalyst comprising platinum, tin, and chlorine supported on alumina spheres is preferred although other catalysts can be substituted. The recycled paraffins together with any feed paraffins charged to the overall process are heated to reaction conditions and preferably passed through a single catalyst bed. The effluent of the catalyst bed is partially condensed to allow a simple separation of a hydrogen-rich gas, a portion of which is withdrawn with the remainder being recycled to the reactor. The net condensate is passed into a stripping column wherein all hydrocarbons having fewer carbon atoms per molecule than the desired feed normal olefin(s) are removed overhead as a light ends stream. Further details on suitable dehydrogenation methods may be obtained by reference to U.S. Pat. Nos. 3,391,218, 3,448,165, 3,745,112, and 3,907,921. The catalyst and the configuration of the dehydrogenation reaction zone may be chosen as desired from any commercially feasible type of catalyst and reactor.

I claim as my invention:

1. In a process for the production of alkylaromatic hydrocarbons in which a feed aromatic hydrocarbon is contacted wiht an acyclic $C_6$-plus olefinic hydrocarbon and liquid phase HF in an alkylation zone at alkylation-promoting conditions to effect the production of the product alkylaromatic hydrocarbon, the resultant alkylation zone effluent separated in a separation zone into a hydrocarbon phase and a denser liquid HF phase, and at least a portion of said denser liquid HF phase regenerated by the removal of high boiling hydrocarbonaceous compounds therefrom; the improvement which comprises introducing the major part of said portion of the denser liquid HF phase from said separation zone into an intermediate point in the height of a regeneration column maintained at regeneration conditions, and passing a smaller part of said portion of the denser liquid HF phase directly from said separation zone into a higher point of said column as reflux therein.

2. A process for the production of linear alkylaromatic hydrocarbons which comprises the steps of:
(a) reacting a feed aromatic hydrocarbon with a $C_6$-plus normal olefinic hydrocarbon in the presence of liquid phase HF having a first purity, and which acts as an alkylation catalyst, in a reaction zone and thereby producing a first hydrocarbon admixture comprising residual feed aromatic hydrocarbon and a product linear alkylaromatic hydrocarbon;
(b) contacting said hydrocarbon admixture with liquid phase HF having a higher second purity in a contacting zone and thereby producing a second hydrocarbon admixture comprising the feed aromatic hydrocarbon and the product linear alkylaromatic hydrocarbon;
(c) passing the second hydrocarbon admixture into a fractionation zone and recovering the product linear alkylaromatic hydrocarbon from the second hydrocarbon admixture; and,
(d) separating liquid phase HF from the reaction zone effluent in a separation zone and regenerating the same in a regeneration column operated at regeneration conditions, with a first aliquot portion thereof passing directly from said separation zone into the top of the regeneration column and a second aliquot portion thereof entering the regeneration column at a lower point in the regeneration column.

3. The process of claim 2 further characterized in that the second portion of the HF entering the regeneration column is at least twice as large as the first portion of HF entering the regeneration column.

4. The process of claim 3 further characterized in that the second portion of the HF enters the regeneration column at a point which is at least three theoretical contacting stages below the top of the regeneration column.

5. The process of claim 4 further characterized in that the normal olefinic hydrocarbon has at least 10 carbon atoms per molecule.

6. The process of claim 5 further characterized in that the feed aromatic hydrocarbon is benzene.

7. A process for the production of alkylaromatic hydrocarbons which comprises the steps of:
(a) admixing a feed aromatic hydrocarbon with an acyclic feed olefinic hydrocarbon which has more than eight carbon atoms per molecule and with liquid phase HF in a reaction zone maintained at alkylation-promoting conditions and thereby forming a reaction zone effluent stream which comprises the feed aromatic hydrocarbon, HF, a product alkylaromatic hydrocarbon and a small amount of high boiling reaction by-products;
(b) separating substantially all of the hydrocarbons present in the reaction zone effluent stream from the liquid phase HF present in the reaction zone effluent stream, and thereby forming a first hydrocarbon stream and a first liquid phase HF stream, passing the thus derived first hydrocarbon stream into a contacting zone wherein the first hydrocarbon stream is contacted with liquid phase HF having a higher purity than the HF which is employed in the reaction zone and thereby forming a contacting zone effluent stream which comprises the feed aromatic hydrocarbon, HF and the product alkylaromatic hydrocarbon;

(c) separating substantially all of the hydrocarbons present in the contacting zone effluent stream from the liquid phase HF present in the contacting zone effluent stream and thereby forming a second hydrocarbon process stream and a second HF stream;

(d) passing a first portion of the second HF stream into the contacting zone and a second portion into the reaction zone;

(e) dividing the first liquid phase HF stream into a first HF recycle stream, which is passed into the reaction zone, and a regeneration HF stream;

(f) passing a first aliquot portion of the regeneration HF stream into an HF regeneration column operated at HF regeneration conditions at the upper end of the regeneration column, and passing a larger second aliquot portion of the regeneration HF stream into the HF regeneration column at a second lower point; and, (g) recovering the product alkylaromatic hydrocarbon from the second hydrocarbon process stream.

8. The process of claim 7 further characterized in that an overhead stream is withdrawn from the HF regeneration column, passed through an overhead condenser and into an overhead receiver, and also further characterized in that a second HF recycle stream is withdrawn from the overhead receiver and passed into the contacting zone.

9. The process of claim 8 further characterized in that the product alkylaromatic hydrocarbon is recovered from the second hydrocarbon process stream by a series of steps which comprises passing the second hydrocarbon process stream into a stripping column, recovering the product alkylaromatic hydrocarbon from a net bottoms stream removed from the stripping column, and also further characterized in that an overhead stream is withdrawn from the stripping column, passed through said overhead condenser and into said overhead receiver, and a hydrocarbon recycle stream, which is rich in the feed aromatic hydrocarbon is withdrawn from said overhead receiver and passed into the reaction zone.

10. The process of claim 9 further characterized in that the feed aromatic hydrocarbon is benzene.

11. The process of claim 10 further characterized in that the acyclic feed olefinic hydrocarbon is a $C_{10}$ to $C_{15}$ normal olefin.

12. The process of claim 11 further characterized in that the acyclic feed olefinic hydrocarbon charged to the reaction zone is a mixture of normal olefinic hydrocarbons and normal paraffinic hydrocarbons.

* * * * *